(12) United States Patent  
Davey et al.

(10) Patent No.: US 7,470,415 B2
(45) Date of Patent: Dec. 30, 2008

(54) METHOD FOR PRODUCING AMMONIA ON THE BASIS OF A NITROGEN-HYDROGEN MIXTURE FROM NATURAL GAS

(75) Inventors: William Davey, Frankfurt (DE); Ermanno Filippi, Castagnola (CH)

(73) Assignees: Lurgi GmbH, Lurglallee, Frankfurt am Main (DE); Ammonia Casale S.A., Via Sorengo, Lugano-Bessom (CH)

( * ) Notice: Subject to any disclaimer, the term of this patent is extended or adjusted under 35 U.S.C. 154(b) by 50 days.

(21) Appl. No.: 10/415,807

(22) PCT Filed: Oct. 24, 2001

(86) PCT No.: PCT/EP01/12254

§ 371 (c)(1), (2), (4) Date: Sep. 10, 2003

(87) PCT Pub. No.: WO02/38499

PCT Pub. Date: May 16, 2002

(65) Prior Publication Data

US 2004/0028595 A1    Feb. 12, 2004

(30) Foreign Application Priority Data

Nov. 10, 2000  (DE) .............................. 100 55 818

(51) Int. Cl.
  *C01C 1/04* (2006.01)
  *C07C 273/04* (2006.01)
(52) U.S. Cl. ..................................... 423/359; 564/69
(58) Field of Classification Search ............ 423/359; 564/69

See application file for complete search history.

(56) References Cited

U.S. PATENT DOCUMENTS

| 3,615,200 A | * | 10/1971 | Konoki ..................... 423/359 |
| 3,720,625 A | * | 3/1973 | Kapp et al. ................ 252/377 |
| 3,872,025 A | | 3/1975 | Singleton |
| 4,181,701 A | | 1/1980 | Topsoe et al. |
| 4,479,925 A | * | 10/1984 | Shires et al. ............... 423/359 |

(Continued)

FOREIGN PATENT DOCUMENTS

DE    32 39 605 A1    4/1984

(Continued)

OTHER PUBLICATIONS

Opposition Brief, no date.

(Continued)

*Primary Examiner*—Wayne Langel

(57) ABSTRACT

A method for producing ammonia from natural gas, fed to an autothermic reformer with an $O_2$ rich gas. Crude synthesis gas is produced at temperatures of 900 to 1200° C., pressures of 40 to 100 bar and in the presence of a cracking catalyst. The crude synthesis gas is led through a catalytic conversion system to convert CO to $H_2$, thereby obtaining a conversion synthesis gas with a $H_2$ content of at least 55 vol.-% and a CO content of not more than 8 vol.-%. The conversion synthesis gas is subjected to a gas purification to remove $CO_2$, CO and $CH_4$, thereby producing an $N_2$—$H_2$ mixture that is subjected to a catalytic ammonia synthesis. The ammonia produced can at least be partially converted to urea by reacting it with $CO_2$.

7 Claims, 2 Drawing Sheets

U.S. PATENT DOCUMENTS

| | | | | |
|---|---|---|---|---|
| 4,671,893 A * | 6/1987 | Pinto | .......................... | 252/376 |
| 4,725,381 A * | 2/1988 | Pinto | .......................... | 252/376 |
| 4,810,417 A * | 3/1989 | Diemer et al. | .............. | 252/373 |
| 4,822,521 A * | 4/1989 | Fuderer | ...................... | 252/376 |
| 4,863,707 A * | 9/1989 | McShea et al. | ............. | 423/359 |
| 5,068,058 A * | 11/1991 | Bushinsky et al. | .......... | 252/376 |
| 5,180,570 A * | 1/1993 | Lee et al. | ..................... | 423/359 |
| 5,252,609 A * | 10/1993 | Pinto | .......................... | 518/703 |
| 5,736,116 A * | 4/1998 | LeBlanc et al. | ............. | 423/359 |
| 5,935,544 A * | 8/1999 | Bhakta | ....................... | 423/359 |
| 6,207,078 B1 * | 3/2001 | Badano | ...................... | 252/373 |

FOREIGN PATENT DOCUMENTS

| | | |
|---|---|---|
| EP | 0 112 613 | 7/1984 |
| EP | 0 307 983 | 3/1989 |
| EP | 0 307 983 A1 | 3/1989 |
| EP | 0 307 983 B1 | 3/1989 |
| EP | 0 905 127 A1 | 3/1999 |
| EP | 0 905 127 B1 | 3/1999 |
| EP | 0 982 266 A2 | 3/2000 |
| EP | 0 999 178 A1 | 5/2000 |
| EP | 1 337 466 | 5/2004 |
| FR | 2 368 435 A1 | 5/1978 |
| GB | 2 048 840 | 12/1980 |
| GB | 2 048 840 A1 | 12/1980 |
| WO | WO 01 09038 | 2/2001 |
| WO | WO 01/09038 A2 | 2/2001 |

OTHER PUBLICATIONS

"Fertilizer Manual", 1998, chapter 9, p. 257, no month.

Hans-Jürgen Arpe, "Ullmann's Encyclopedia of Industrial Chemistry", 1985, p. 174-185.

*Mineral Fertilizer Production and the Environment*, Technical Report No. 26-Part 1, "The Fertilizer Industry's Manufacturing Processes and Environmental Issues", p. 1-24, no date.

Hydrocarbon Processing, Mar. 1994, Petrochemical/ Chemical Developments "Improve syngas production using autothermal reforming", p. 39-46.

Max Appl Ammonia "Principles and Industrial Practice", Wiley-VCH, 1999, no month.

J.R. Rostrup-Nielsen "Production of synthesis gas", Catalysis Today, 18 (1993) 305-324, Elsevier Science Publishers B.V., Amsterdam, no month.

B.M. Tindall et al. "Alternative technologies to steam-methane reforming", Hydrocarbon Processing, Nov. 1995, p. 75-80.

Falbe J. et al. Chemie, Rompp Lexikon, "Natural Gas", p. 1193-1194, no date.

\* cited by examiner

METHOD FOR PRODUCING AMMONIA ON THE BASIS OF A NITROGEN-HYDROGEN MIXTURE FROM NATURAL GAS

This application is a 371 of PCT/EP01/12254, filed on Oct. 24,2001.

The invention relates to a process for the catalytic production of ammonia from a nitrogen/hydrogen mixture.

The production of an ammonia synthesis gas is known from German patent 2007441 wherein a raw gas is produced by gasifying hydrocarbons, this raw gas being desulfurized, converted, freed from $CO_2$ and finally subjected to a liquid nitrogen wash to remove residual impurities. A similar process is described in EP patent 0307983 wherein converted synthesis gas is submitted to a liquid nitrogen wash upstream of the ammonium synthesis. Details of the catalytic production of ammonia are to be found in Ullmann's Encyclopedia of Industrial Chemistry, $5^{th}$ edition, volume A2, pages 143-215; the production of urea is described there in volume A27, pages 333-350. A process for the combined production of ammonia and urea is outlined in EP-A-0905 127.

The objective of the invention is to operate the ammonia synthesis process at a low cost and to provide a method which is well suited for large plants. In accordance with the invention, this is achieved by routing natural gas—jointly with $O_2$-rich gas—to an autothermal reformer where, at temperatures in the range of 900-1200° C., a pressure of 40 to 100 bar and in the presence of a reforming catalyst, raw synthesis gas is produced which, on a dry basis, exhibits an $H_2$ content of 55-75% (vol.), a CO content of 15-30% (vol.) and a $CO_2$ content of 5-30% (vol.), at an $H_2$:CO volume ratio of 1.6-4, the raw synthesis gas being extracted from the autothermal reformer, cooled, routed through a catalytic converter to convert $CO+H_2O$ into $CO_2 +H_2$ and extracting converted synthesis gas with an $H_2$ content, on a dry basis, of not less than 55% (vol.) and a $CO_2$ content of not more than 8% (vol.), submitting the converted synthesis gas to a multistage gas wash for removing $CO_2$, CO and $CH_4$, producing an $N_2$-$H_2$ mixture which is passed to an ammonia synthesis unit for the catalytic production of ammonia.

It is important for the process to do without a plant for steam reforming for producing the raw synthesis gas. The autothermal reformer can be operated at relatively high pressures in the range of 30-100 bar, preferably 40-80 bar. Downstream of the reformer, this high pressure can virtually be maintained so that prior to entering the ammonia synthesis unit, the gas only has to be slightly compressed. This is much less cost intensive than conventional methods including steam reforming which only allow relatively low pressures. Autothermal reformers have another advantage over steam reforming in that they supply gas at an appropriate $H_2$/$CO_2$ ratio so that, after conversion with the $CO_2$ accruing in the gas wash, the entire $NH_3$ produced can be converted to urea.

A favorable, advanced embodiment consists in converting the ammonia produced in the ammonia synthesis unit at least partly to urea by conversion with $CO_2$. It is of advantage in this context that $CO_2$ is removed from the converted synthesis gas in at least one gas washing stage and used for producing urea. One of several possibilities is the combined process described in EP-A-0905 127. Under normal circumstances, the $CO_2$ obtained in the gas washing stage is absolutely sufficient to meet the $CO_2$ demand of the urea synthesis, in contrast to conventional processes.

The $CO_2$ is preferably removed from the converted gas mixture by means of a physical wash process e.g. operated with methanol at temperatures from −20 to −70° C. In this process, only a relatively small amount of energy, including compression energy, is consumed. At the same time, at least half of the $CO_2$ can be recovered in the regeneration of the washing liquid at pressures e.g. in the range of 2-8 bar so that compression energy is saved in the subsequent application of $CO_2$ for the production of urea.

Conveniently, the $O_2$-rich gas supplied to the autothermal reformer should have an $O_2$ content of not less than 70% (vol.), preferably at least 90% (vol.). In this way, the content of impurities in the raw synthesis gas is reduced and the gas washing stage can be designed smaller.

Embodiment options of the process are explained with the aid of the drawing.

Figure 1:
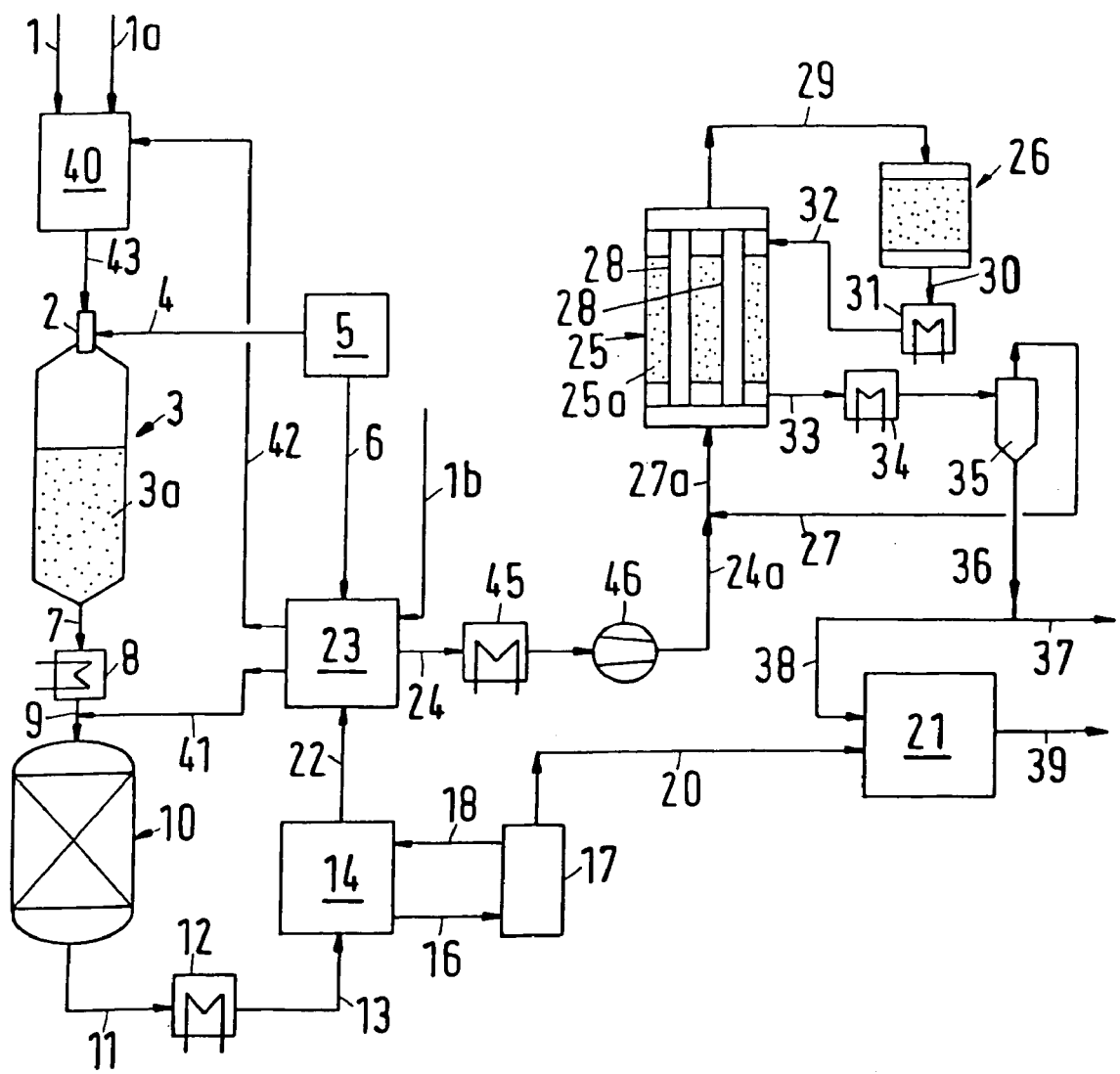
FIG. 1 shows a process flow diagram.

According to FIG. 1, the pretreatment unit (40) is fed with natural gas through line (1) and water vapor through line (1a) in order to carry out the desulfurization, heating and removal of the $CO_{2+}$ components according to the state of the art. The pretreatment unit (40) is also fed with methane-containing gas through line (42). A mixture primarily consisting of methane and water vapor flows through line (43) to the burner (2) of an autothermal reformer (3) and simultaneously, through line (4), $O_2$-rich gas with an $O_2$ content of usually 70% (vol.), but preferably not less than 95% (vol.), is supplied. The $O_2$-rich gas originates from an air separation plant (5). The reformer (3) contains a fixed bed (3a) of a state-of-the-art granular reforming catalyst on nickel basis, for example. In the reactor, a pressure in the range of 30-100 bar, preferably 40-80 bar, prevails whilst the temperatures are in the range of 900-1200° C. The raw synthesis gas extracted through line (7) exhibits an $H_2$ content of 55-75% (vol.), a CO content of 15-30% (vol.), a $CO_2$ content of 5-30% (vol.) and an $H_2$:CO volume ratio of 1.6-4. After cooling in heat exchanger (8), the raw synthesis gas is fed through line (9) to a shift conversion stage (10) which may also consist of several reactors. A temperature range of 150-500° C. and preferably 280-450° C. is applied using state-of-the-art catalysts on iron basis, for instance. $CO+H_2O$ are catalytically converted to $CO_2+H_2$. The gas in line (11) preferably has an $H_2$:$CO_2$ volume ratio of 2.5-3 (dry basis).

The converted synthesis gas withdrawn through line (11) has an $H_2$ content, on a dry basis, of not less than 55% (vol.) and preferably at least 65% (vol.) as well as a $CO_2$ content of not more than 8% (vol.). This gas is initially passed through an indirect cooling stage (12), being subsequently fed through line (13) to a gas washing unit (14) in order to remove $CO_2$ in particular. This can be effected, for example, by a physical wash with methanol at temperatures in the range of about −70 to −20° C., options being, for example, a methyl diethyl amine wash or the Selexol wash. Spent $CO_2$-containing washing solution is withdrawn through line (16) and routed to a regenerator (17) in order to remove the $CO_2$ from the wash solution. Regenerated wash solution is returned to the gas wash (14) through line (18). The accruing $CO_2$ is excellently suited for being fed to a urea synthesis unit (21) through line (20).

Partly purified synthesis gas is withdrawn from the gas wash (14) through line (22) and treated in a second wash unit (23) where liquid nitrogen acts as the washing liquid. The nitrogen needed to this end comes from the air separation unit (5), being supplied through line (6). Details of the liquid nitrogen wash for producing $NH_3$ synthesis gas are to be found in EP patent 0307983 as mentioned above. Typically, the washing unit (23) produces a CO-containing gas which is returned to the shift conversion stage (10) through line (41). If a $CH_4$-rich gas is produced simultaneously, it is returned through line (42). In order to support refrigeration, a natural gas stream at a pressure of 10 to 100 bar and preferably not less than 30 bar is supplied through line (1b). This stream is allowed to expand in the wash plant (23) in order to accomplish a pressure reduction by at least 8 bar, preferably not less than 25 bar. The expanded natural gas may then be extracted, likewise through line (42), for example.

The wash (23) is controlled such that the synthesis gas accumulating in line (24) already exhibits a molar $H_2$:$N_2$ ratio of about 3:1. This synthesis gas is heated up in an indirect heat exchanger (45), compressed in compressor (46) and flows through line (24a) to an ammonia synthesis unit which includes the indirectly cooled reactor (25) and the adiabatic reactor (26). Recirculated synthesis gas from line (27) together with the fresh synthesis gas from line (24a) at temperatures in the range of 100-200° C. enters, through line (27a), reactor (25) from where it flows through the heat transfer tubes (28) or ducts, with the gas acting as a cooling fluid and removing heat from the catalyst bed (25a). Alternatively, boiling water can be used as a cooling fluid in the ammonia synthesis.

The synthesis gas leaves the reactor (25) through line (29) at temperatures in the range of 300-500° C., contacting the catalyst bed when arriving in reactor (26). The $NH_3$ forming reaction is exothermal so that the mixture leaving through line (30) exhibits temperatures of 400-600° C., thus having to be passed through a cooler (31). Subsequently, the $NH_3$-containing synthesis gas, arriving through line (32), enters reactor (25) and flows through its indirectly cooled catalyst bed. The outlet temperature through line (33) is in the range of 300-500° C. and preferably 380-430° C. The product mixture in line (33) has an $NH_3$-concentration of not less than 20% (vol.) and additionally contains mainly $N_2$ and $H_2$. This mixture is submitted to multistage cooling (34), subsequently passing on to a separator (35) from which raw $NH_3$ is withdrawn in liquid state through line (36). The gaseous components are extracted through line (27) and returned as recycle gas.

The raw $NH_3$ produced can be removed totally or partly through line (37) and routed to state-of-the-art use. Moreover, the raw $NH_3$ may be totally or partly sent to a state-of-the-art urea synthesis unit through line (38). The urea produced is withdrawn through line (39).

Figure 2:
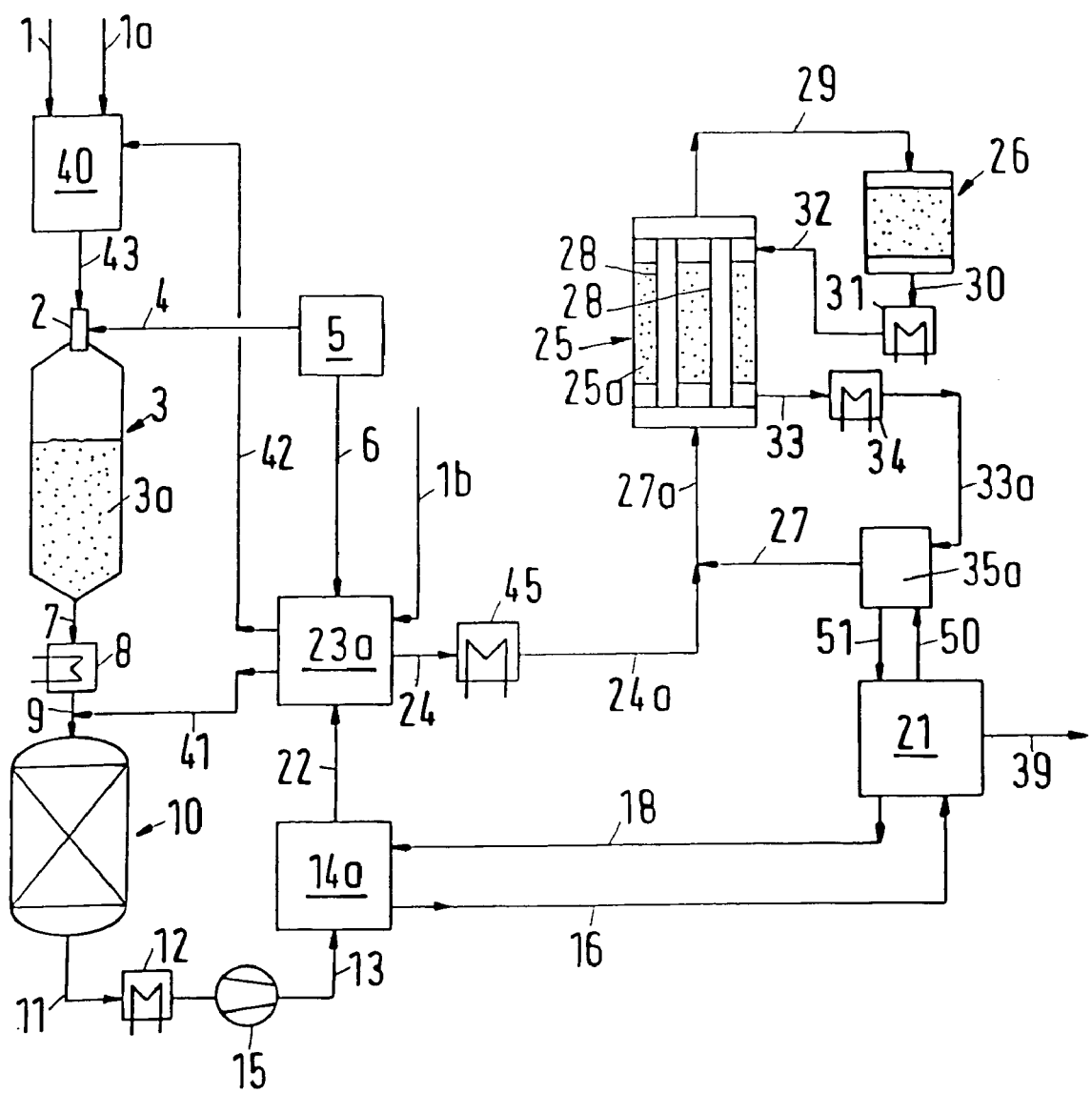
FIG. 2 shows a flow diagram of an alternative process

In the process according to FIG. 2, the synthesis gas coming from the shift conversion stage (10) though line (11) is passed through an indirect cooling stage (12), compressed in the compressor (15) and fed to a $CO_2$ absorber (14a) through line (13). In the absorber, $CO_2$ is removed using a weak carbamate solution which is supplied through line (18) and originates from the urea synthesis unit. Spent $CO_2$-laden wash solution is drawn from line (16) and fed to the synthesis (21). The partially purified synthesis gas flows through line (22) to the fine screening unit (23a) which can be designed e.g. as a liquid nitrogen washing system, as a pressure swing adsorption plant or as a catalyst methanation system. Line (1b) is only suited for the liquid nitrogen wash.

The ammonia synthesis is operated as described for FIG. 1. The product mixture coming from the cooling stage (34) is routed through line (33a) to an adsorber (35a) where $NH_3$ is washed out from line (50) by means of water. The $NH_3$-containing water is fed to the urea synthesis stage (21) via line (51); details are described in EP-A-0905 127. As for the rest, the reference figures of FIG. 2 have the same meaning as explained for FIG. 1.

The process according to the invention has the following main advantages over known processes:

1. Steam reforming is not needed, meaning that a large and expensive plant unit can be omitted. Another advantage is that higher pressures can be applied for cracking methane and other hydrocarbons than would be viable with steam reforming.
2. Preferably, the nitrogen needed for the $H_2$-$N_2$ synthesis gas is only added in the liquid-nitrogen wash and does not have to be carried by the gas through the upstream hydrogen production and purifying stages.
3. In the liquid-nitrogen washing stage, methane gas can conveniently also be separated and returned to the autothermal reformer. This allows the reformer to be operated at very low temperatures of about 950° C. without having to ensure that the gas mixture produced in the reformer is methane-free. Furthermore, a natural gas stream supplied at a pressure of 10 to 100 bar may be expanded in the wash unit using liquefied nitrogen, for refrigeration purposes (Joule-Thompson effect).
4. In the wash with liquid nitrogen, conveniently a CO-rich gas stream is also produced which is returned to the CO conversion stage. A residual CO content in the converted gas mixture is therefore not detrimental and may amount up to 8% (vol.), mostly not more than 4% (vol.). As a consequence, it is feasible to use sturdy and low-cost iron catalysts for shift conversion so that more sensitive copper catalysts are not needed.
5. Gas cleaning by means of a liquid nitrogen wash yields an ultra-pure $H_2$-$N_2$ synthesis gas so that bleeding of part of the recycle gas from the $NH_3$ synthesis can be omitted, totally or for the most part.
6. The waste heat produced is sufficient to cover the total energy demand including compression energy for the $NH_3$ synthesis and subsequent urea synthesis.
7. The consumption of natural gas, referred to the net calorific value, is only about 27.3 GJ/t for $NH_3$ production and not more than about 19 GJ/t for urea production, which is extremely low compared with the known processes. This natural gas consumption has been taken as a basis for the following example.
8. The plant for the process can be modularized and can be erected on a relatively small area of land.

EXAMPLE

The process configuration considered is as depicted in FIG. 1, wherein 3000 t of ammonia or 5263 t of urea may be produced per day. The following data have been partly calculated.

Through line (1), natural gas and through line (1a) water vapor are supplied in accordance with a molar water vapor: carbon ratio of 2.55. The data relating to quantities, temperatures, pressures and gas compositions (in % (vol.)) are as listed in Table I:

TABLE I

| Reference figure | 1 | 43 | 7 | 11 | 24a | 27a | 33 | 20 |
|---|---|---|---|---|---|---|---|---|
| Rate (t/h) | 92 | 263 | 336 | 357 | 127 | 382 | 382 | 162 |
| Temperature (° C.) | 25 | 65 | 95 | 32 | 168 | 175 | 403 | 32 |
| Pressure (bar) | 55 | 61 | 60 | 57 | 137 | 143 | 140 | 3 |
| Composition | | | | | | | | |
| $CH_4$ | 91.3 | 27.0 | 1.8 | 2.0 | — | — | — | 0.8 |
| $C_2H_6$ | 5.8 | — | — | — | — | — | — | — |

TABLE I-continued

| Reference figure | 1 | 43 | 7 | 11 | 24a | 27a | 33 | 20 |
|---|---|---|---|---|---|---|---|---|
| CO | — | 1.6 | 10.6 | 1.1 | — | — | — | — |
| $CO_2$ | 1.9 | 0.6 | 7.1 | 16.7 | — | — | — | 99.0 |
| Ar | — | — | 0.3 | 0.5 | — | — | — | 0.1 |
| $H_2$ | — | 3.2 | 38.7 | 47.5 | 74.8 | 70.8 | 54.1 | 0.1 |
| $N_2$ | 1.0 | 0.3 | 0.4 | 2.3 | 25.2 | 24.4 | 18.9 | — |
| $H_2O$ | — | 67.3 | 41.1 | 29.9 | — | — | — | — |
| $NH_3$ | — | — | — | — | — | 4.8 | 27.0 | — |

The oxygen in line (4) has an $O_2$ content of 95% (vol.). The synthesis gas in line (24) contains less than 5 ppm (vol.) CO and about 25 ppm (vol.) Ar. The NiO catalyst (3a) and the catalysts for the $NH_3$ synthesis are commercial grade (e.g. manufactured by Süd-Chemie, Munich (DE), Type G-90 and AS-4). The reformer (3) is operated at an outlet temperature of 950° C., the level corresponding to the lowest total gas consumption.

The shift conversion stage (10) comprises first a gas-cooled reactor of similar design to reactor (25), followed by an intermediate cooler and an adiabatic reactor with catalyst bed. The conversion catalyst is a commercial-grade Fe—Cr catalyst (Type G-3C from Süd-Chemie). The residual CO content of the converted gas is only 1.6% (vol.) (calculated dry), the $H_2:CO_2$ volume ratio being 2.84 (calculated dry).

For the gas wash units (14, 17), the Rectisol process is applied where $CO_2$ is removed with methanol at −58° C. In the liquid nitrogen wash (23), the synthesis gas is initially cooled to −185° C. whereby $CH_4$ is condensed, separated and removed through line (42).

In contact with liquid $N_2$, the $CO_2$ content is condensed, separated and passed through line (41) to the conversion stage. The composition of the stream in lines (41) and (42) is shown in Table II (in % (vol.)).

TABLE II

|  | (41) | (42) |
|---|---|---|
| $CH_4$ | 5.13 | 52.54 |
| CO | 21.18 | 12.27 |
| $CO_2$ | — | 0.53 |
| Ar | 7.18 | 8.64 |
| $H_2$ | 9.76 | 6.75 |
| $N_2$ | 56.75 | 19.27 |

In the cooling system (34), 65% of the $NH_3$ produced is liquefied by applying cooling water. A part stream (purge gas) is withdrawn to remove impurities from the recycle gas of the $NH_3$ synthesis unit.

What we claim is:

1. A process for the catalytic production of ammonia from a nitrogen/hydrogen mixture comprising:
   (a) passing natural gas, an $O_2$ rich gas containing at least 95% vol. of $O_2$ and water vapor to a reforming zone comprised of an autothermal reformer, wherein said autothermal reformer comprises a burner;
   (b) reforming, in said autothermal reformer, in the presence of a reforming catalyst said natural gas, $O_2$ rich gas and water vapor at a temperature in the range of 900-1200° C. and a pressure of 40-100 bar to produce a raw synthesis gas comprising an $H_2$ content of 55-75 vol. %, a CO content of 15-30 vol. %, a $CO_2$ content of 5-30 vol. %, and an $H_2:CO$ volume ratio of 1.6-4;
   (c) extracting and cooling said synthesis gas from said autothermal reformer;
   (d) passing said cooled synthesis gas through a shift conversion zone for convening CO $+H_2O$ into $CO_2+H_2$, wherein the converted synthesis gas has an $H_2$ content of 55 vol. % or greater and a CO content of 8 vol. % or less;
   (e) contacting said converted synthesis gas with liquid nitrogen in a multi stage gas washing process, wherein $CO_2$, CO and $CH_4$ are removed from the convened synthesis gas and an $N_2$—$H_2$ mixture is produced; and
   (f) feeding said $N_2$—$H_2$ mixture to an ammonia synthesis plant for the catalytic production of ammonia.

2. A process as claimed in claim 1, wherein $CO_2$ is removed from the converted synthesis gas in a physical wash with methanol at temperatures in the range of −70 to −20° C.

3. A process as claimed in claim 1, wherein CO— containing gas is separated from the synthesis gas in a gas washing stage operated with liquid nitrogen and passed on to catalytic conversion.

4. A process as claimed in claim 1, wherein the $N_2$—$H_2$ mixture is routed through at least two catalyst-containing reactors in the ammonia synthesis unit where the $N_2$—$H_2$ mixture serves as a cooling fluid in a reactor for indirect catalyst cooling.

5. A process as claimed in claim 1, wherein the synthesis gas leaving the shift conversion stage exhibits an $H_2:CO_2$ volume ratio of 2.5-3.0 (calculated dry).

6. A process for the catalytic production of ammonia from a nitrogen/hydrogen mixture comprising:
   (a) passing natural gas, an $O_2$ rich gas containing at least 95% vol. of $O_2$ and water vapor to a reforming zone comprised of an autothermal reformer, wherein said autothermal reformer comprises a burner;
   (b) reforming, in said autothermal reformer, in the presence of a reforming catalyst said natural gas, $O_2$ rich gas and water vapor at a temperature in the range of 900-1200° C. and a pressure of 40-100 bar to produce a raw synthesis gas comprising an $H_2$ content of 55-75 vol. %, a CO content of 15-30 vol. %, a $CO_2$ content of 5-30 vol. %, and an $H_2:CO$ volume ratio of 1.6-4;
   (c) extracting and cooling said synthesis gas from said autothermal reformer;
   (d) passing said cooled synthesis gas through a shift conversion zone for convening $CO+H_2O$ into $CO_2+H_2$, wherein the converted synthesis gas has an $H_2$ content of 55 vol. % or greater and a CO content of 8 vol. % or less;
   (e) contacting said converted synthesis gas with liquid nitrogen in a multi stage gas washing process, wherein $CO_2$, CO and $CH_4$ are removed from the convened synthesis gas and an $N_2$—$H_2$ mixture is produced, wherein the removed $CO_2$ is recovered at least partly and used for urea production; and
   (f) feeding said $N_2$—$H_2$ mixture to an ammonia synthesis plant for the catalytic production of ammonia, wherein the ammonia is at least partly convened to urea with $CO_2$.

7. A process for the catalytic production of ammonia from a nitrogen/hydrogen mixture comprised of:
   (a) passing natural gas, an $O_2$ rich gas containing at least 95% vol. of $O_2$ and water vapor to a reforming zone comprised of an autothermal reformer, wherein said autothermal reformer comprises a burner;
   (b) reforming, in said autothermal reformer, in the presence of a reforming catalyst said natural gas, $O_2$ rich gas and water vapor at a temperature in the range of 900-1200° C. and a pressure of 40-100 bar to produce a raw synthesis gas comprising an $H_2$ content of 55-75 vol. %, a CO content of 15-30 vol. %, a $CO_2$ content of 5-30 vol. %, and a CO volume ratio of 1.6-4;

(c) extracting and cooling said synthesis gas from said autothermal reformer;

(d) passing said cooled synthesis gas through a shift conversion zone for converting $H_2$+CO into $CO_2$+$H_2$, wherein the converted synthesis gas has an $H_2$ content of 55 vol. % or greater and a CO content of 8 vol. % or less;

(e) contacting said converted synthesis gas with liquid nitrogen in a multi stage gas washing process, wherein $CO_2$, CO and $CH_4$ are removed from the converted synthesis gas and an $N_2$—$H_2$ mixture is produced, wherein a natural gas stream at a pressure of about 10 to 100 bar is routed to a gas wash unit operated with liquid nitrogen in which the pressure of said natural gas stream is reduced by at least 8 bar; and (f) feeding said $N_2$—$H_2$ mixture to an ammonia synthesis plant for the catalytic production of ammonia.

\* \* \* \* \*

UNITED STATES PATENT AND TRADEMARK OFFICE
CERTIFICATE OF CORRECTION

PATENT NO. : 7,470,415 B2 Page 1 of 1
APPLICATION NO. : 10/415807
DATED : December 30, 2008
INVENTOR(S) : William Davey et al.

It is certified that error appears in the above-identified patent and that said Letters Patent is hereby corrected as shown below:

Title page, Item [73], the Assignee's address,
"Lurglallee"

Should read

Lurgiallee

Signed and Sealed this

Twentieth Day of October, 2009

David J. Kappos
*Director of the United States Patent and Trademark Office*